United States Patent [19]

Pieters et al.

[11] Patent Number: 4,638,106
[45] Date of Patent: Jan. 20, 1987

[54] TWO STAGE PROCESS FOR IMPROVING THE CATALYST LIFE OF ZEOLITES IN THE SYNTHESIS OF LOWER OLEFINS FROM ALCOHOLS AND THEIR ETHER DERIVATIVES

[75] Inventors: Wim J. M. Pieters, Morristown, N.J.; Yoshiharu Okumura, Tokyo, Japan

[73] Assignee: Exxon Research & Engineering Co., Florham Park, N.J.

[21] Appl. No.: 769,357

[22] Filed: Aug. 26, 1985

Related U.S. Application Data

[62] Division of Ser. No. 630,636, Jul. 13, 1984, Pat. No. 4,554,260.

[51] Int. Cl.$^4$ .............................................. C07C 1/00
[52] U.S. Cl. .................................. 585/640; 585/408; 585/733
[58] Field of Search ........................................ 585/640

[56] References Cited

U.S. PATENT DOCUMENTS

4,358,395 11/1982 Haag et al. ........................... 585/640
4,477,585 10/1984 Kaeding .................................. 502/77

FOREIGN PATENT DOCUMENTS

1203740 10/1965 Fed. Rep. of Germany ........ 502/85
43230 4/1981 Japan ..................................... 502/85

*Primary Examiner*—Curtis R. Davis
*Attorney, Agent, or Firm*—R. A. Maggio; F. A. Sinnock

[57] ABSTRACT

A process for improving the catalyst life of zeolites employed in the conversion of alcohols (e.g. methanol) and/or their ether derivatives (e.g. dimethyl ether) wherein a suitable zeolite is modified in a 2-stage procedure by providing a controlled low amount of a coke precursor deposit on the external surface of the zeolite, and then heating this treated zeolite in an inert gas at specifically controlled temperatures for a minimum time is disclosed. A process of employing this modified zeolite to produce lower olefins is also disclosed.

11 Claims, No Drawings

TWO STAGE PROCESS FOR IMPROVING THE CATALYST LIFE OF ZEOLITES IN THE SYNTHESIS OF LOWER OLEFINS FROM ALCOHOLS AND THEIR ETHER DERIVATIVES

This is a division of application Ser. No. 630,636, filed July 13, 1984, now U.S. Pat. No. 4,554,260.

BACKGROUND OF THE INVENTION

This invention relates to acidic shape selective zeolite catalysts which have been pretreated to enhance catalyst life and methods for their use to synthesize olefins, in particular by conversion of lower monohydric alcohols and/or their ether derivatives.

Olefins, especially ethylene and propylene, are used on a large scale as intermediates for the manufacture of staple products such as olefin polymers, ethylene oxide, non-ionic detergents, glycols and fiber-forming polyesters. Processes for producing olefins usually involve non-catalytic pyrolysis of volatile hydrocarbons such as natural gas liquids or petroleum distillates. Catalytic pyrolysis processes have been proposed but do not appear to have reached industrial use.

In countries where such volatile hydrocarbons are not accessible but such feedstocks as coal, oil shale and methane, and consequently carbon monoxide/hydrogen synthesis gas derived therefrom, are available, it would be desirable to produce olefins from synthesis gas. It has been proposed to do this by converting the synthesis gas to methanol or to hydrocarbons and/or their oxygenated derivatives and reacting such products over shape selective acidic zeolites, e.g., of the ZSM-5 family. (See for example U.S. Pat. Nos. 3,894,106; 4,025,571; and 4,052,479).

Shape selective zeolite materials, both natural and synthetic, have been demonstrated in the past to have catalytic capabilities for various types of organic compound conversions. These materials are ordered porous crystalline metasilicates (e.g. aluminosilicates) having a definite crystalline structure within which there are a large number of cavities and channels, which are precisely uniform in size. Since the dimensions of these pores are such as to accept, for adsorption, molecules of certain dimensions while rejecting those of larger dimensions, these materials are deemed to possess the property of shape selectivity, have been referred to as "molecular sieves", and are utilized in a variety of ways to take advantage of these properties.

Such shape selective molecular sieves include a wide variety of positive ion-containing crystalline aluminosilicates, both natural and synthetic. Aluminosilicates can be described as a rigid three-dimensional network of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra-containing aluminum is balanced by the inclusion in the crystal of a cation, for example an alkali metal or an alkaline earth metal cation. This can be expressed by formula wherein the ratio of Al to the number of various cations, such as Ca/2, Sr/2, Na, K or Li is equal to unity. One type of cation may be exchanged either in entirety or partially by another type of cation utilizing ion exchange techniques in a conventional manner. By means of such cation exchange, it has been possible to vary the size of the pores in a given aluminosilicate by suitable selection of the particular cation. The spaces between the tetrahedra are occupied by molecules of water prior to dehydration.

A preferred group of shape selective crystalline aluminosilicates, designated as those of the ZSM-5 type (e.g. see U.S. Pat. No. 3,702,886) as well known for use in the synthesis of olefins from syn gas derived materials such as methanol. Other shape selective zeolite materials are also well known for this purpose as discussed in the aforedescribed patents. Characteristic of any shape selective catalyst capable of catalyzing the conversion of methanol and/or dimethyl ether to higher hydrocarbons is its possession of acid sites which are believed to be responsible for catalytic activity. The acidity characteristics of such shape selective zeolites are believed to be related to the amount of alumina in the zeolite (see U.S. Pat. No. 3,941,871), e.g., it is generally recognized that the lower the alumina content of the zeolite the lower the overall relative acidity of the zeolite.

Unfortunately, the use of acidic shape selective zeolites to catalyze methanol and/or dimethyl ether conversion for olefin production is not entirely satisfactory because such zeolites are also well known to catalyze the formation of higher hydrocarbons such as $C_5+$ paraffins, aromatics and alkylated aromatics. The particular distribution of products obtained from the use of any given catalyst is typically controlled by the reaction conditions, particularly temperature. Thus, while there is not a clear line of demarcation in product distribution as a function of temperature, it has been recognized (for example, see U.S. Pat. No. 3,894,107) that as the reaction temperature is increased, the methanol conversion can be shifted in favor of the formation of ethers, olefins, aromatics and alkylated aromatics at respectively higher reaction temperatures. The use of temperature control to influence product distribution is illustrated in U.S. Pat. Nos. 4,052,479 and 4,058,576 wherein staging of the reactions is employed. The partial pressure of the reactant feed has also been observed to influence olefin selectivity. Thus, U.S. Pat. No. 4,025,576 discloses the use of a subatmospheric partial pressure of the reactant feed to improve its conversion with enhanced olefin selectivity. Subatmospheric partial pressure of the reactant feed is obtained either by maintaining a partial vacuum in the conversion zone, or by co-feeding a diluent. Suitable diluents include any substantially inert substance that is a gas or vapor at reaction temperature such as steam, as well as nitrogen, carbon dioxide, carbon monoxide, and the like. When such diluents are used, total pressure in the reaction zone may range from subatmospheric up to about 1500 psia depending on the amount of diluent introduced with the feed. The diluent serves to assist in removing the heat of reaction generated in the more exothermic alcohol or ether conversions. Typical reaction temperatures vary from 500° to 1000° F. (260° to 537° C.).

In addition to controlling reaction conditions, product distribution favoring olefin production can be influenced substantially by modifications in the acidic shape selective zeolite catalyst. Thus, various cations can be used for modification by exchange as illustrated by U.S. Pat. Nos. 4,079,096 and 4,066,714.

U.S. Pat. No. 3,911,041 discloses a phosphorus modified zeolite prepared by reacting the latter with a phosphorus containing compound having a covalent or ionic substituent capable of reacting or exchanging a hydrogen ion. The phosphorus containing zeolite is described as possessing a greater number of acid sites than the parent zeolite but these more numerous acid sites appear to have a lesser acid strength than those found in the unmodified zeolite. It is suggested that the replacement of the strong acid sites in the parent zeolite, with a greater number of relatively weak acid sites may be responsible for blocking the aromatizing activity of the unmodified zeolite. A further increase in the number of weak acid sites is said to be effected by contact of the zeolite with water vapor, preferably prior to use of the zeolite as a catalyst and subsequent to phosphorus modification. The location of the strong acid sites is unspecified. The phosphorus modified zeolite is alleged to enhance the selectivity to light olefins and decrease the selectivity to aromatics. Olefin selectivities (ethylene, propylene and butene) disclosed include 38.4% at a methanol conversion of 85% (Table 1, Run 2); and 43–70% at conversions greater than 75% (Table 4). At 300° C. reaction temperature, and 0.22% of DME conversion, the olefin selectivity is 100% (Table 6). This selectivity drops as the temperature is increased to 350° C. (% olefin selectivity 49.8 at a 5.7% DME conversion) and drops further as the reaction temperature increases to 400° C. (% olefin selectivity 45.0% at 56.7% conversion) as also disclosed in Table 6. Table 10 discloses DME conversions ranging from 3.6 to 100% at olefin selectivities which vary between 12.7% and 73.4%.

Kikuchi et al suggest in the article "Acid Properties of ZSM-5 Type Zeolite and its Catalytic Activity in Methanol Conversion" J. Japan. Petrol. Inst. Vol. 25, No. 2, pp. 69–73 (1982) that poisoning the acid sites located at the external surface or around the entrance to the pores of a ZSM-5 type zeolite with 4-methyl quinoline inhibits aromatic hydrocarbon production from methanol, and conclude that such acid sites participate in the formation of aromatic compounds such as trimethyl benzene and tetramethyl benzene. Such poisoning with 4-methyl quinoline is a result of neutralization of acid sites with a base and is not due to coke formation.

European Patent Application Publication No. 54,375 discloses a process for converting a methanol containing feed to hydrocarbons including olefins using a shape selective zeolite such as the ZSM-5 type, both modified and unmodified, as well as dealuminized mordenites, and faujasite. A promoter is incorporated into the reactant feed to accelerate the conversion of methanol to hydrocarbons, particularly olefins, which permits the use of reaction temperatures less severe than those associated with prior art processes needed to achieve similar conversions, thereby leading to enhanced olefin selectivity attributable to the use of such lower reaction temperatures (page 7, lines 2 et seq). Suitable promoters include aromatic hydrocarbons and their precursors, olefins and their precursors, and aldehydes, e.g., formaldehyde. In the case of ZSM-5 type zeolites the Al content is varied from 0 to 4%, the lower limit to Al content being embodied in a composition referred to as silicalite, e.g., $SiO_2:Al_2O_3$ mole ratio of 1600:1.

Notwithstanding the prior art processes for enhancing olefin selectivity, such methods inevitably are accompanied by complex side reactions such as aromatization, polymerization, alkylation and the like to varying degrees. As a result of these complex reactions, a carbonaceous deposit is laid down on the catalyst which is referred to by petroleum engineers as "coke". The deposit of coke on the catalyst tends to seriously impair the catalyst efficiency for the principal reaction desired, and to substantially decrease the rate of conversion and/or the selectivity of the process. Thus, it is common to remove the catalyst from the reaction zone after coke has been deposited thereon and to regenerate it by burning the coke in a stream of oxidizing gas. The regenerated catalyst is returned to the conversion stage of the process cycle. The period of use between catalyst regenerations is often referred to as catalyst life. There are obvious economic incentives to improve the catalyst life such as the savings in capital investment to achieve regeneration, such as for example, the installation of a fluid bed reactor system, or a multiple bed reactor system. Furthermore, a rapidly deactivating catalyst produces a product distribution which changes substantially with time, thereby complicating the downstream purification operation.

It has been observed (see U.S. Pat. No. 3,941,871) that while lowering the aluminum content of a shape selective zeolite will reduce coke formation, excessive reduction in the alumina content will destroy the activity of the zeolite catalyst responsible for olefin production.

An alternative approach to coping with the coke formation problem is to employ a fluidized bed wherein the coked catalyst can be continuously regenerated. At least one fluidized system intentionally maintains a high coke level between about 5 and 20% by weight of the catalyst, as disclosed in U.S. Pat. No. 4,328,384. This patent discloses the use of a fluidized bed riser reaction scheme for the production of gasoline range boiling products, wherein the catalyst particles are segregated into a lower disperse fluidized phase, and an upper dense fluidized phase. The methanol feed is converted to dimethyl ether and olefins in the lower disperse catalyst phase. The olefins from the lower disperse phase are then converted to gasoline range boiling products in the upper dense phase. This reaction scheme is employed to provide minimum contact of the methanol with the final desired products, particularly aromatics, since methanol and aromatics react to form tetramethyl benzene (durene), an undesirable component in gasoline. The catalyst employed in this reactor scheme is regenerated under conditions sufficient to achieve only a partial removal of coke therefrom rather than provide a clean, burned catalyst. Maintaining a high coke level on the catalyst in the range of 5 to 20 weight percent, reduces the catalyst activity, and olefins are preferentially produced for a given space velocity under selected temperature conditions. While methanol conversions up to about 70% are alleged to be obtainable in this manner (Col. 12, line 32) only about 7% of the product from the disperse phase comprises $C_2$ to $C_5$ olefins (Col. 13, line 66). Lowering the coke level during regeneration increases catalyst activity, but at the expense of $C_2$ to $C_5$ olefin selectivity. The catalyst is withdrawn from the dense upper phase for regeneration and it can be transported to the regeneration zone with an inert gas or with the regeneration gas of desired $O_2$ concentration (Col. 13, lines 25 et seq). The regenerated catalyst is introduced into the upper dense phase from which is withdrawn catalyst that is introduced into the disperse lower phase for olefin production. Thus, the coke content of the catalyst when it enters the disperse phase is even higher than the freshly regenerated catalyst due to the additional coke deposits which form while the catalyst is in the high aromatics containing dense phase prior to removal therefrom and introduction into the lower disperse phase. The use of such excessive amounts of coke on the olefin producing catalyst is believed to be responsible for such lower catalyst activity.

Precoking of a zeolite catalyst used for the alkylation of aromatic compounds is disclosed in U.S. Pat. No. 4,276,438 (Col. 13, lines 24 et seq). The effect of the precoking is undisclosed.

U.S. Pat. No. 4,229,608 is directed to a cyclic heat balanced process for converting methanol and/or dimethyl ether to a product rich in ethylene and propylene and containing less than 20 weight percent methane, using a fluidized zeolite catalyst at temperatures of between about 425° and 760° C. (e.g., 800° to 1200° F.). During the conversion reaction less than 9 (e.g., 4 to 6) weight percent of the feed is converted to a carbonaceous deposit (coke) on the zeolite amounting to between about 0.4 and 1 weight percent of the zeolite. The mixture of spent zeolite catalyst and hydrocarbon product are separated and the spent fluidized zeolite catalyst regenerated by combustion in air at temperatures of between about 650° and 760° C. and the carbonaceous deposit removed therefrom (see Col. 2, lines 11 et seq). At Col. 2, lines 18 et seq, it is noted that water generated as a by-product in the conversion reaction had been observed to cause a substantial loss of activity of crystalline aluminosilicate zeolites by steaming. The cyclic heat balanced operation disclosed in this patent is alleged to increase the stability of the zeolites employed therein. At Col. 2, lines 26 et seq, it is concluded that under the specified conditions of short contact time and controlled temperature, the hydrocarbon sorbed product and/or the residual carbonaceous deposit, remaining on the catalyst after regeneration, may serve to protect the catalytic sites of the zeolite. The amount, if any, of residual carbonaceous deposit on the zeolite allegedly remaining after regeneration is undisclosed. Furthermore, the regenerated catalyst is not subjected to a heat conditioning step prior to introduction back into the conversion zone.

U.S. Pat. No. 4,231,899 is directed to a method for producing a steam stable aluminosilicate zeolite catalyst. In accordance with this process a zeolite, containing organic cations and/or in contact with a charring agent is calcined at a temperature below 1100° F. (593° C.), e.g. 800° to 1050° F. (i.e. 426° to 565° C.) to convert a portion of the organic cations and/or charring agent to a carbonaceous material and deposit at least 1.5–15 wt.% thereof within the pores of the zeolite. Fresh uncoked catalyst is said to possess much more activity (e.g. excessive active sites) than is required for the conversion of oxygenated hydrocarbons. The precoking procedure of this patent is therefore asserted to protect these excess active sites from steam deactivation until such time that they can be revived during regeneration (Col. 2, Lines 36 et seq). It will be observed that the precoking procedure is conducted (in the presence of oxygen, Col. 8, Line 24, as contrasted to conventional techniques, Col. 10, Line 33) for 16 hours or more, and no heat treatment as defined herein is employed subsequent to the precoking procedure. It is further observed that the coke formed during precoking is deposited "within" the pores of the zeolite (Col. 8, Lines 55 et seq).

U.S. Pat. No. 4,358,395 is directed to a process for converting lower monohydric alcohols and ether derivatives thereof with a precoked crystalline aluminosilicate zeolite. Catalyst precoking is conducted by exposing the zeolite to a thermally decomposable organic compound at a temperature in excess of the decomposition at a temperature e.g. generally greater than 1000° F. (538° C.), but less than 1200° F. (649° C.) at a hydrogen to organic compound mole ratio between 0 and 1, to deposit at least 1% coke, predominantly on the surface of the zeolite (Col. 9, Lines 57 et seq). When precoking temperatures are less than 1100° F. (593° C.) at least 0.2 mole of $H_2$ per mole of organic compound is employed (Col. 6, Lines 55 et seq). Suitable thermally decomposable organic compounds include paraffinic, cycloparaffinic, olefinic, cycloolefinic, and aromatic compounds, as well as oxygen containing compounds such as alcohols, aldehydes, ketones, ethers, and phenols. Preferably, the organic compound is the same as that subsequently undergoing conversion (Col. 7, Line 5). An additional optional treatment either before or after precoking involves contact of the catalyst with steam. This patent distinguishes the coke deposited pursuant to precoking (referred to as selectivity enhancing coke), and coke deposited during the hydrocarbon conversion reaction (referred to as activity reducing coke). During regeneration in a hydrogen containing atmosphere, the activity reducing coke is removed, while the selectivity enhancing coke is not. The precoked catalyst is alleged to be suitable for a wide variety of hydrocarbon conversion reactions, including the conversion of lower monohydric alcohols and ethers to olefins, although this reaction is not illustrated in the examples, the only reactions illustrated by example being limited to toluene disproportionation and toluene alkylation. It will be observed that precoking times illustrated in the examples range from 16 to 112 hours at precoking temperatures of no less than 1050° F. (565° C.). Furthermore, this patent fails to show a heat treatment as defined herein, subsequent to precoking.

In view of the above, there has been a continuing search for ways to improve catalyst life while still attaining acceptable, and most preferably, improved olefin selectivity and/or yield. The present invention was developed in response to this search.

SUMMARY OF THE INVENTION

It has been found that the life and/or selectivity of acidic shape selective zeolites can be improved substantially when these catalysts are employed for the conversion of alcohols and/or ethers to lower olefins by a controlled hydrocarbon pretreatment procedure followed by further heat conditioning of the pretreated catalyst with an inert gas prior to using the conditioned catalyst to produce olefins. Without wishing to be bound by any particular theory, it is believed that the hydrocarbon pretreatment procedure described herein results in a deposition, on the exterior surface of, and around to entrance to, the zeolite pores, of what is believed to be a coke precursor consisting of a polymeric carbonaceous material having a high hydrogen to carbon ratio, in very small amounts. A zeolite having a coke precursor derived from methanol deposited thereon absent the heat conditioning step performs substantially the same as the untreated zeolite. It is concluded from this observation that the acid sites on which the coke precursor are deposited are available for catalytic reaction and the zeolite still possesses an active surface. However, it has also been found that the heat conditioning step described herein changes the nature of the coke precursor, and the extent and effect of this change is a function of the heat conditioning temperature. More specifically, it is believed that the coke precursor can be selectively converted to coke in a conventional sense (e.g. low hydrogen to carbon ratio), with the degree of this conversion being disproportionate relative to the strong and weaker acid sites when the heat conditioning step is controlled as described herein. In this manner a much greater degree of coke formation is believed to be achieved on the strong acid sites relative to the weaker acid sites. Thus, the heat conditioning step of the present invention is believed to selectively deactivate the strong acid sites of the zeolite surface to a much greater extent than the weaker acid sites. Apparently, very little deactivation of the essential weaker acid sites occurs during the 2 step treatment of the present invention. This selective deactivation of strong acid sites is significant because it is the strong acid sites which are believed to be primarily responsible for subsequent coke formation, as well as the undesired by-products, produced during the hydrocarbon conversion process, while it is the weaker acid sites which are responsible for the desired catalytic effect. The overall effect of the 2 step treatment is to substantially increase catalyst life while improving, or at least maintaining, olefin selectivity. If the heat conditioning temperature is too high, the selectivity in the deactivation of the acid sites is lost and substantial drop in desired catalytic activity is observed.

Accordingly, in one aspect of the present invention there is provided a process for modifying a crystalline metalosilicate shape selective acidic zeolite free of coke deposits thereon, wherein said metal of the metalosilicate is selected from the group consisting of aluminum, gallium, and mixtures thereof, to improve the catalyst life thereof when said modified zeolite is used to convert, a hydrocarbon feed comprising at least one member selected from the group consisting of monohydric alcohols having from 1 to about 4 carbon atoms, ethers derived from said alcohols, and mixtures thereof, to an olefin containing product at a conversion reaction temperature of from about 300° to about 350° C., which zeolite, prior to said modification, is: (a) capable of catalyzing said hydrocarbon conversion reaction; (b) has a channel size and structure such as to permit (i) entry of the hydrocarbon feed into the zeolite and diffusion to the active acid sites within the zeolite, and (ii) formation of olefin products within said zeolite and diffusion of said products out of the zeolite; and (c) hydrothermally stable at a temperature of at least 290° C.; which process comprises:

(A) contacting said zeolite with a coke precursor forming hydrocarbon feed for a period of from about 0.5 to about 4 hours, said coke precursor forming hydrocarbon feed being (i) comprised of at least one member selected from the group consisting of monohydric alcohols having from 1 to about 4 carbon atoms, ethers derived from said alcohols, olefins having from about 1 to about 5 carbon atoms, and mixtures thereof; and (ii) heated to a temperature of from about 320° to about 350° C.; and (B) contacting the zeolite treated in accordance with Step (A), with an inert gas heated to a temperature of from about 350° to about 425° C. for a period of at least 1 hour.

In another aspect of the present invention, there is provided a process for employing the aforedescribed modified zeolite in the synthesis of olefins.

DESCRIPTION OF PREFERRED EMBODIMENTS

The reactions conducted in accordance with the process of the present invention are well known for synthesizing olefins. Such reactions can be broadly characterized by the condensation of certain feed materials to form hydrocarbon mixtures rich in light olefins, e.g., $C_1$ to $C_5$, preferably ethylene and propylene. Suitable feeds for this reaction include any monohydric alcohol having from 1 to 4 carbon atoms and/or ethers derived from these alcohols. Thus, methanol, ethanol, n-propanol, isopropanol, n-butanol, sec-butanol and iso-butanol may be used either alone or in admixture with one another, or in admixture with ethers derived from such alcohols. Likewise, as noted, ethers such as methylethyl ether and dimethyl ether may be similarly used. Particularly preferred feeds are methanol, dimethyl ether and mixtures thereof.

The alcohols employed in the feed may be manufactured from synthesis gas, i.e., a mixture of CO and $H_2$, obtained from coal or manufactured from a petroleum fraction in excess supply, or they may be produced by fermentation.

The zeolite suitable for modification herein may be any crystalline zeolite of natural or synthetic origin which (a) is capable of converting the alcohol and/or ether derivatives thereof described above to olefinic hydrocarbons in the absence of the pretreatment and heat conditioning steps described herein; (b) has a channel size and structure such as to permit (i) entry of the reactants in the feed to the active acid sites within the zeolite and (ii) formation of olefin products within the zeolite and diffusion of these products out of the zeolite; and (c) is hydrothermally stable under the hydrocarbon reaction conditions described herein, e.g., at temperatures of at least 290° C. and preferably at least 325° C.

The classes of acidic shape selective zeolite materials capable of catalyzing the aforedescribed reactions which are subjected to the hydrocarbon pretreatment and heat conditioning described herein are well known in the art. These materials typically are characterized by a crystal structure such as to provide constrained access to and egress from the intracrystalline free space of the zeolites by virtue of having pores, the major dimension of which is, typically greater than 3, preferably greater than 5 Angstroms. The particular pore size and pore window size will vary in part depending on the arrangement of the oxygen atoms in the zeolite. Zeolites suitable for modification herein have thus been further characterized as possessing 8-, preferably 10-membered rings of oxygen atoms.

Zeolites possessing 8-membered rings include by way of example, erionite, chabazite, zeolite-T, zeolite ZSM-34 and zeolite ZK-5. Zeolite T is described in U.S. Pat. No. 2,950,952; zeolite ZSM-34 is described in U.S. Pat. No. 4,079,095; and zeolite ZK-5 is described in U.S. Pat. No. 3,247,195 the disclosures of which are herein incorporated by reference. Such zeolites are characterized by pore dimensions between about 3 and about 6 Angstroms and pore windows as would be provided by 8-membered rings of oxygen atoms present in these zeolites. These pores may be circular as in the case of zeolite ZK-5 (e.g. pore diameter about 3.9 Angstroms) or somewhat elliptical such as in erionite having pores of about 3.6 by 5.2 Angstroms.

The preferred zeolites for use herein possess 10-membered rings of oxygen atoms as exemplified by ZSM-5 type zeolites described in U.S. Pat. No. 3,702,886 the disclosure of which is herein incorporated by reference. Such zeolites typically have a pore dimension of greater than about 5 Angstroms.

Other zeolites of the ZSM-5 type suitable for use herein include ZSM-11 described in U.S. Pat. No. 3,709,979; ZSM-12 described in U.S. Pat. No. 3,832,449; ZSM-21 and ZSM-38 described in U.S. Pat. Nos. 4,046,859 and 4,148,713; ZSM-23 described in U.S. Pat. No. 3,076,842; HZSM-5 described in U.S. Pat. No. 4,083,889; ZSM-5/ZSM-11 described in U.S. Pat. No. 4,148,713; and ZSM-48 described in U.S. Pat. No. 4,300,011, the disclosures of all of the above patents being incorporated by reference.

Although zeolites possessing 12-membered rings of oxygen in theory would not offer sufficient constraint to produce advantageous conversions, excessive puckering such as present in TMA offretite and/or pore blockage may under these circumstances be sufficiently restrictive to exhibit some constrained access. Thus, other 12-ring structures may exist which may be operative for other reasons. It will be understood that the ringed structures referred to above are those formed by the regular disposition of the tetrahedra making up the anionic framework of the crystalline aluminosilicate, the oxygen atoms themselves being bonded to the silicon or aluminum atoms at the centers of the tetrahedra.

While the above theoretical structural considerations are conventional and useful means for characterizing zeolites suitable for catalyzing the conversion of reactants described herein to light olefins, it is not the present intention to judge the suitability of the zeolites for use herein in terms of their shape selectivity (i.e. constrained access and egress properties), solely on the basis of such considerations. An alternative and conventional way of expressing such properties is in terms of the Constraint Index of the zeolite. The definition and description of the method of determination of Constraint Index is provided in U.S. Pat. No. 4,025,571 the disclosure of which is herein incorporated by reference. The Constraint Index approximates the ratio of the cracking rate constants for hexane and 3-methylpentane. Conventionally, zeolites possessing a Constraint Index of from about 1 to about 12 have been preferred for the hydrocarbon conversion reactions described herein and such zeolites have been designated as possessing the appropriate shape selectivity designated for catalysis of these reactions.

An important chemical property which characterizes the zeolites employed for the purposes described herein is the acidity of the zeolite. The acidity of the zeolite is determined by ammonia adsorption. This test is conducted using a TGA/DSC analyzer to determine the amount of ammonia chemisorbed, under temperature conditions to be used in the intended hydrocarbon conversion reaction, e.g. 290° to 350° C. Accordingly, the acidity of the unmodified zeolite is controlled to impart an ammonia adsorption thereto of typically from about 30 to about 120, and preferably from about 50 to 100 mmoles of $NH_3$ per gram of catalyst.

If the acidity of the unmodified zeolite is too high, the activity of the catalyst will be too high resulting in the formation of excessive amounts of higher molecular weight products such as $C_4$ to $C_{10}$ hydrocarbons.

However, if the acidity of the zeolite is too low the catalyst lacks flexibility in activity needed to adjust to variations in reaction conditions such as reaction temperature and residence time.

While acidity of the zeolite is generally associated with the metal atoms (e.g. aluminum or gallium) present therein, this acidity can also be significantly influenced by cations, e.g., metal cations, associated with these aluminum atoms in a final zeolite having a low alumina content. For example, when Na is present as a cation in the zeolite it will have a quenching effect on the acidity of the same. Consequently, the acidity of an acid quenching metal cation containing zeolite will be less than the corresponding hydrogen form thereof at equal aluminum contents. The degree of this quenching effect, while negligable at high aluminum content, is believed to increase substantially at the low alumina contents most suitable for the olefin synthesis reaction. Thus, at low alumina contents minor variations in the metal cation content of the zeolite can cause major shifts in the acidity of the zeolite and the resulting catalyst performance. As a first approximation, therefore, it is believed that the acidity of the zeolite can be viewed as resulting, at least in part, from (a) the absolute amount of aluminum and/or gallium present in the zeolite, and (b) the balance established between the aluminum and/or gallium and the associated cation content of the zeolite. It is this balance in conjunction with the overall aluminum and/or gallium content and the acidity resulting therefrom, which influences the selection of an appropriate silica to alumina ratio in the zeolite. For example, in making this selection, the moles of alumina in the silica to alumina mole ratio present in an aluminosilicate zeolite is controlled to impart an appropriate effective aluminum content to the zeolite. The effective aluminim content of the zeolite (effective in terms of the aluminum's contribution to the acidity of the zeolite) is defined herein to be the moles of aluminum in the zeolite, minus the moles of associated acid quenching cation multiplied by the valence of said cation, in a zeolite crystal structure having an aluminum content of typically from about 0.2 to about 1.5%, and preferably from about 0.3 to about 0.5%, by weight, based on the weight of the zeolite. From a practical standpoint, when the alumina content of the zeolite exceeds about 1.5%, the distinction between actual and effective silica alumina ratios can be ignored. However, for olefin synthesis, the alumina content is preferably controlled to fall within the 0.2 to 1.5% range described above. The most common acid quenching cations typically present in the zeolite are the alkali and alkaline earth metal cations, particularly sodium and potassium. Hydrogen is not considered to be an acid quenching cation. A silica to alumina ratio calculated on the basis of the effective aluminum content is referred to as the effective silica to alumina ratio. Similar considerations apply with respect to gallium containing silicates. Furthermore, if the acid quenching cation is present in only impurity amounts, e.g. less than about 30 ppm metal cation based on the weight of the zeolite, the effect of these acid quenching cations can be ignored and the effective and actual silica:alumina ratios are considered to be the same.

Accordingly, one way to impart the aforedescribed acidity to the zeolite is to control the calculated value of the effective silica to alumina ratio to be typically from about 100:1 to about 400:1, preferably from about 150:1 to about 300:1, and most preferably from about 175:1 to about 250:1. The effective silica to alumina mole ratio is controlled by adjusting the actual silica to alumina ratio and/or the acid quenching cation content of the zeolite appropriately. The actual silica to alumina ratio referred to above may be determined by conventional analysis. This ratio is meant to represent as closely as possible, the ratio in the rigid anionic framework of the zeolite crystal and to exclude aluminum in the binder or in cationic or other form within the channels. The zeolites suitable for modification herein may be in the hydrogen form or they may be base exchanged or impregnated to contain ammonium or a metal cation complement. It is desirable to calcine the catalyst after base exchange.

When synthesized in the alkali (e.g. Na) metal form, the zeolite is conveniently and preferably converted to the hydrogen form, generally by intermediate formation of the ammonium form as a result of ammonium ion exchange and calcination of the ammonium form to yield the hydrogen form. In general, it is contemplated that more than 80 percent and preferably more than 95 percent of the cationic sites of the crystalline aluminosilicate zeolite, above described, will be occupied by hydrogen ions.

In addition to the hydrogen form, other forms of the zeolite wherein the original alkali metal can be reduced to less than about 1.5 percent by weight may be used. Thus, the original alkali metal of the zeolite may conventionally be replaced by ion exchange with other suitable ions of Groups Ia, IIa, Ib, IIb, IIIb, IVb, Vb and VIII of the Periodic Table as provided in Cotton and Wilkinson "Advanced Inorganic Chemistry", 3rd ed. (1972). By way of example, such ions include K, Cs (Group Ia); Mg, Ca, (Group IIa); Cu (Group Ib); Zn (Group IIb); B, Ga (Group IIIb); Ge (Group IVb); P (Group Vb); and Fe, N (Group VIII).

The zeolites suitable for modification herein also include gallosilicates wherein the aluminum in the zeolite crystalline framework of the zeolites described herein is replaced completely or partially with gallium. Accordingly, representative crystalline gallosilicate zeolites suitable for use herein are described in U.S. Pat. Nos. 3,702,886; 4,245,130; U.K. patent application No. 2,023,562, published Jan. 3, 1980 and European Patent Publication No. 55,044 published June 30, 1982, the disclosures of which are herein incorporated by reference. Such gallosilicates for purposes of the present invention typically are synthesized to possess an effective silica to gallia mole ratio, to impart the aforedescribed acidity thereto, of typically from about 1:400 to about 1:100, preferably from about 1:300 to about 1:150, and most preferably from about 1:250 to about 1:150.

The most preferred zeolites employed for modification herein are of the ZSM-5 type, but which have been prepared on an alkali and/or alkaline earth metal free basis using active pH control with an acid to adjust the pH of reaction mixture to be from about 10 to about 12. The details of this preparation are provided in commonly assigned U.S. patent application Ser. No. 630,723, filed July 13, 1984 by A. Bortinger E. Suciu and W. Pieters, the disclosure of which is herein incorporated by reference. Since this type of preparation produces the hydrogen form of the zeolite directly, the effective and actual silica/alumina ratios are considered the same.

Upon selecting a suitable zeolite capable of converting alcohols and/or their ether derivatives to olefins, and, for a freshly prepared zeolite, prior to conducting said hydrocarbon conversion reactions, the zeolite is subjected to a 2-stage modification to improve catalyst life. Catalyst life is defined herein to be the period of continuous use of the zeolite for the hereindescribed hydrocarbon conversions at any given set of reaction conditions before regeneration of the zeolite to remove coke deposits is required. Generally, regeneration is required when the yield of desired product drops below economically acceptable levels.

In the first stage of the catalyst modification, the zeolite is typically treated in a manner and under conditions sufficient to provide a deposit of coke precursor on the external surface thereof in an amount typically less than about 1%, preferably less than about 0.75%, and most preferably less than about 0.5%, by weight, based on the weight of deposit and the weight of the zeolite.

Thus, by controlling (e.g., minimizing) the amount of coke precursor deposited on the zeolite surface through the conditions described hereinafter, it is possible to prepare the zeolite surface for selective deactivation of the acid sites located at the surface of the zeolite with the heat conditioning step while simultaneously avoiding blockage of the pores of the zeolite. Furthermore, the size of the pore channels within the zeolites described herein are selected such that the formation of coke precursor within the interior channels of the zeolite is substantially avoided. For example, in the reactions under consideration, it is believed that coke precursor formation progresses through a series of reactions wherein light olefins, such as ethylene and propylene (in the case of a methanol and/or DME feed), are formed initially which then polymerize to $C_4$ to $C_6$ hydrocarbons that cyclize to aromatics, which in turn are alkylated and polymerized to a carbonaceous material (i.e. coke precursor) having a high hydrogen to carbon gram atom ratio, e.g. typically about 1. It is characteristic of the zeolites described herein, particularly of the ZSM-5, 10-membered ring type, that the space available within the interior pore channels is insufficient to permit the aforedescribed polymerization of aromatics in the final stages of coke precursor formation to occur over the short time of the precoking treatment. Thus, not only is pore blockage of the zeolite avoided by the controlled precoking treatment, but the internal acid sites of the zeolite are maintained in substantially the same condition as existing prior to precoking.

The deposition of coke precursor can conveniently be carried out by contacting the zeolite with a hydrocarbon, preferably a vaporized thermally decomposable hydrocarbon, capable of being converted, preferably quickly, to a carbonaceous deposit having the aforedescribed high hydrogen content. The deposition is conducted by heating said hydrocarbon in contact with the zeolite to a temperature of from about 320° to about 350°, and preferably from about 330° to about 340° C., for a period of from about 0.5 to about 4, preferably from about 1 to about 2 hours.

If the hydrocarbon treatment temperature is too high, excessive deposits will occur in the form of coke precursor and/or coke itself (a carbonaceous material with a low hydrogen to carbon ratio), causing blockage of the pores of the zeolite, and the subsequent performance of the zeolite as a catalyst will suffer. If the temperature is too low, little coke precursor is formed with little apparent benefit.

While any hydrocarbon capable of forming coke precursor deposits in the manner and over the period described may be employed, typical suitable coke precursor forming hydrocarbons are those which form any intermediate compound in the coke precursor forming process. The selection of a particular hydrocarbon from this latter class is influenced by the rate at which such compound is converted to the coke precursor. As this reaction rate is increased, it becomes increasingly difficult to control and stabilize the reaction from fluctuations in such process variables as reaction temperature, flow rates and the like, thereby rendering it difficult to control the degree as well as the identity of the deposit. Thus, when the coke precursor formation is viewed as a series of reactions as described above, the degree of preference, for the selection of a compound participating in this sequence as the precursor forming hydrocarbon, increases, as one progresses down the reaction sequence toward the initial reactants, i.e. alcohol and/or ether. Accordingly, the $C_1$ to $C_4$ alcohols and/or ether derivatives thereof, described above for use in the hydrocarbon conversion feed gas are suitable, as are olefins, preferably monoolefins, having from about 1 to about 10, preferably from about 1 to about 5 carbons. Unsubstituted aromatic compounds can be employed but are less preferred while alkylaromatics are least preferred.

Representative examples of suitable coke precursor forming hydrocarbons include ethylene, propylene, butene, methanol, dimethyl ether, propanol, butanol and mixtures thereof.

The most preferred coke precursor forming hydrocarbons include methanol, dimethyl ether and mixtures thereof.

Contact of the zeolite with the coke precursor forming hydrocarbon to effect deposition is preferably conducted in the vapor phase by passing a moving gaseous stream of the coke precursor forming hydrocarbon over the zeolite heated to the aforedescribed temperatures. Contact time of the coke precursor hydrocarbon feed with the zeolite is controlled to achieve a WHSV of typically from about 1 to about 8, preferably from about 2 to about 5, and most preferably from about 3 to about 5 $hr^{-1}$.

The pressure of the coke precursor hydrocarbon feed is typically controlled to assure that this feed is a vapor at the selected conversion temperature and can be subatmospheric, atmospheric or superatmospheric. The preferred coke precursor forming reaction pressures range typically from about 0.5 to about 1.5, and preferably from about 0.9 to about 1.2 atmospheres at STP. It is desirable to exclude oxygen, halogens and hydrogen from the coke precursor hydrocarbon forming feed.

The coke precursor forming procedure is preferably performed at least on the fresh zeolite which possesses the ability to catalyze the formation of olefins, e.g., subsequent to the activation or calcination heat treatments conventionally employed on zeolites intended for use in synthesizing olefins, but prior to encountering the alcohol and/or ether reactant feed stream at reaction conditions described hereinafter. However, it is also contemplated that the zeolite which is modified herein can also be derived from spent zeolite catalyst which has been deactivated by the deposition of coke during the hydrocarbon conversion reaction to produce olefins. Such spent zeolite must first be regenerated however. Regeneration of the zeolite is typically conducted by combustion of the coke in an oxygen containing gas, such as air, at temperatures of typically from about 450° to about 600°, preferably from about 475° to bout 575°, and most preferably from about 500° to about 550° C.

Accordingly, the 2-stage modification of the present invention can employ spent zeolite therein by initially effecting substantially complete regeneration of the zeolite to remove the coke present thereon. This completely regenerated zeolite is then employed in the first stage of the zeolite modification and contacted with the coke precursor forming hydrocarbon to deposit the appropriate amount of coke precursor thereon for the heat conditioning step.

The coke precursor modified zeolite provided in accordance with the first step of the treatment is then subjected to heat conditioning treatment by contact with an inert gas in a manner and under conditions sufficient to increase the catalyst life of the zeolite relative to the absence of the heat conditioning treatment.

The coke precursor deposit resulting from the first stage of treatment is present in sufficiently minor amounts and is believed to contain sufficient residual acidic protons that the strong and weaker acid sites present on the underlying surface of the zeolite are still capable of exerting their catalytic effect. Since a desired catalytic effect (e.g. enhanced olefin selectivity) is attributable to the weaker acid sites, while an undesired catalytic effect is attributable to the strong acid sites in the form of enhanced high molecular weight product selectivity, and enhanced coke formation, little has been achieved after the first stage of treatment to supress the undesired catalytic effect. While not wishing to be bound by any particular theory, it is believed that when the coke precursor modified zeolite is contacted with an inert gas at elevated temperature in the second stage of treatment, the gas functions as a heat transfer medium and causes the coke precursor to selectively react in the close vicinity of the strong acid sites producing coke having a very low residual acidic proton content present therein. In contrast, it is believed that the coke precursor overlying weaker acid sites retains its high residual proton content and the desired catalytic effect exerted thereby is preserved. In short, the delicate control of the 2-stage treatment of the present invention has enabled the utilization of the much greater propensity of the strong acid sites to catalyze coke formation as a self deactivating mechanism for selective passivation of these sites. Generally, the heat conditioning temperature must be not less than, and is preferably greater than, the hydrocarbon conversion reaction temperature selected to be used in conjunction with the conditioned zeolite and not greater than about 420° C.

Accordingly, while any effective heat conditioning temperature and time may be employed for the above purpose, it is contemplated that such a heat treatment be conducted at a temperature of typically at least about 350° C., for a period of at least 1 hour, and generally will be conducted at inert gas temperatures of typically from about 350° to about 425°, preferably from about 375° to about 410°, and most preferably from about 390° to about 410° C., for periods of at least 1 hour, and typically from about 1 to about 8, preferably from about 2 to about 6, and most preferably from about 2 to about 4 hours. The higher the heat conditioning temperature the shorter will be the minimum period of treatment. It will be understood that reaction induced by the inert gas on the zeolite surface is exothermic and in a fixed bed system, the bed temperature will likely exceed the temperature of incoming inert gas. However, it has been found that control of the incoming inert gas temperatures specified above is effective to produce the desired selective passivation of the zeolite. As the heat conditioning treatment temperature of the inert gas is decreased below the above ranges the observable effect on catalyst life and selectivity decreases significantly. However, if the heat conditioning temperature is too high, e.g. above 500° C., the catalyst activity is significantly impared.

The duration of the heat conditioning treatment is critical in that if too short a period is employed no relative improvement in catalyst life will be observed. There is no limit, other than economic considerations, on the maximum period of the heat treatment.

The gas used for the heat conditioning treatment, as described above, must be inert under the conditions of the heat treatment. By "inert" in this context is meant the gas should not be reactive at least with the catalyst, or the precursor forming hydrocarbons employed in the first stage.

Representative inert gases suitable for use in the heat conditioning step include nitrogen, helium, argon, carbon dioxide, methane and mixtures thereof. Molecular oxygen, water, halogens, as well as the alcohol and/or ether reactant feed gases are not inert and should be excluded from the scope of the conditioning gas.

The heat conditioning step can be conducted in any manner which results in intimate contact between the zeolite and the conditioning gas. Accordingly, the conditioning gas is typically passed as a moving stream over the zeolite at a contact time with the zeolite sufficient to achieve a WHSV of typically from about 1 to about 200, preferably from about 10 to about 100, and most preferably from about 20 to about 50 $hr^{-1}$.

The pressure of the inert gas during the conditioning step is not critical and typically can vary from about 0.5 to about 100, preferably from about 0.9 to about 1.0, and most preferably from about 1 to about 5 atmospheres at STP.

It may be desirable in some instances to incorporate the zeolite, prior or subsequent to the 2-stage modification described above, in another material resistant to the temperatures and other conditions employed in the conversion process. Such matrix materials include synthetic or naturally occurring substances as well as inorganic materials such as clay, alumina or other metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state or originally mined or initially subjected to calcination, acid treatment or chemical modification.

In addition to the foregoing materials, the zeolites employed herein, either prior or subsequent to the 2-stage modification, may be composited with a porous matrix material, such as alumina, silica-alumina, silica-magnesia, silica-zirconia, silica-thoria, silica-berylic, silica-titania as well as ternary compositions, such as silica-alumina-thoria, silica-alumina-zirconia. The matrix may be in the form of a cogel. The relative proportion of finely divided zeolite and inorganic oxide gel matrix may vary widely with the zeolite content ranging from between 1 to about 99 percent by weight and more usually in the range of about 5 to about 80 percent by weight of the composite. The preferred matrix material is inert such as alpha-alumina, silica or very weakly acidic materials which do not interfere with the catalytic process.

Furthermore, while not preferred, the conditioned zeolite can be admixed with unmodified zeolite for use in the hydrocarbon conversion process although it is preferred that all the zeolite catalyst employed in such reactions be modified in accordance with the aforedescribed procedures.

The process of this invention for using the modified zeolites described herein is preferably conducted such that alcohol and/or ether conversion is carried out in the vapor phase by contact in a reaction zone, such as for example, a fixed bed of catalyst, under effective conversion conditions, said catalyst being characterized as above-defined.

The alcohol and/or ether hydrocarbon conversion process described herein may be carried out as a batch type, semi-continuous or continuous operation utilizing a fixed or moving bed catalyst system. Thus, one embodiment entails use of a catalyst zone wherein the alcohol and/or ether charge is passed concurrently or countercurrently through a moving bed of particle-form catalyst. The latter, after use, is conducted to a regeneration zone wherein coke is burned from the catalyst in an oxygen-containing atmosphere, e.g. air, at an elevated temperature, after which the regenerated catalyst is recycled to the 2-stage treatment conditioning zones and then the conversion zone for further contact with the alcohol and/or ether feed.

The hydrocarbon feed gas may optionally also contain diluents including any substantially inert substance that is a gas or vapor at reaction temperature. Gaseous nitrogen, carbon dioxide, and carbon monoxide are examples of such materials. Alkanes having up to 3 carbon atoms such as methane, ethane and pentane may also be employed as diluents, while $C_4$ and higher carbon number alkanes are undesirable since they are more rapidly converted to coke.

Other hydrocarbon feed additives, which preferably are used in conjunction with an alcohol, e.g. methanol feed, are aromatic hydrocarbon selectivity promoters. Such aromatic promoters include benzene, $C_1$ to $C_5$ (e.g. $C_1$ to $C_2$) alkyl mono or poly substituted benzenes, para-xylene, toluene, and mixtures thereof. The aromatic hydrocarbon promoters are chosen to be of such a size as to be adsorbed into and diffuse within the zeolite pores. While they preferably are reactive towards Bronsten acids they should not irreversibly neutralize the same. The preferred aromatic promoters include benzene, para-xylene and toluene.

The inclusion of the aromatic promoters in an alcoholic feed results in a significant enhancement in olefin selectivity with a moderate drop in conversion at constant reaction conditions relative to the absence of the promoters. It has been discovered, that the inclusion of such aromatic promoters in the feed for use in conjunction with a zeolite subjected to the 2-stage modification described herein, significantly dimishes the benefits of this 2-stage treatment vis-a-vis catalyst life. However, it has also been discovered that the inclusion of water (e.g. as steam) in the methanol/aromatic hydrocarbon feed restores, at least in part, the catalyst life enhancement while preserving the selectivity enhancement.

Accordingly, while any amount of aromatic promoter effective to improve the olefin selectivity from methanol may be employed in the hydrocarbon feed, it is contemplated that such effective amount constitute a mole ratio of aromatic promoter to methanol of typically from about 0.2:1 to about 0.01:1, preferably from about 0.1:1 to about 0.02:1, and most preferably from about 0.7:1 to about 0.04:1.

Likewise, while any amount of water can be employed to improve the catalyst life relative to the absence of said water in the feed, it is contemplated that such effective amount constitute a molar ratio of methanol to water of typically from about 1:0.05 to about 1:0.5, preferably from about 1:0.7 to about 1:0.33 and most preferably from about 1:0.1 to about 1:0.2.

The method of adding the aromatic promoter to the process reactor is not critical and will be readily determined by those skilled in the art. Where the aromatic promoter is miscible with a methanol/water feed in the desired proportions it may be simply incorporated into the feed through suitable conventional mixing means before the methanol/water feed is vaporized for introduction into the reactor. Where methanol and water are fed separately to the reactor, the aromatic promoter may also be fed independently or may be mixed first with one of the other feed components, typically methanol, prior to entry into the reactor. An inert carrier gas, typically nitrogen, may also be used to introduce the aromatic promoter.

When dimethyl ether is employed as the reactant in the feed gas either in the presence, and particularly in the absence of methanol, it is preferred to initially include steam in the feed gas. More specifically, the molar ratio of dimethyl ether to steam is typically controlled to be from about 1:5 to about 1:0.2, preferably from about 1:2 to about 1:0.5, and most preferably from about 1:0.7 to about 1:1.2 for a period of typically from about 2 to about 24, preferably from about 4 to about 10, and most preferably from about 5 to about 8, under the hereindescribed reaction conditions. It is most preferred that conditioned catalyst be contacted first with steam alone for a period of typically from about 1 to about 10, and preferably from about 2 to about 5 at the hereindescribed reaction temperatures and conditions. It has been found that initial contact of the conditioned zeolite with large amounts of DME in the hydrocarbon feed in the absence of water tends to diminish catalyst life by hastened coke deposition. Alternatively, where a mixture of methanol and DME is employed in the reaction feed, it is preferred, in lieu of the initial steam treatment, to optionally initially introduce methanol alone, for the aforedescribed steam conditioning periods, prior to introducing the methanol/DME feed mixture.

If too much steam is present in the feed, it will tend to undesirably decoke the zeolite.

When methanol along is employed as the reactant in the feedstream in the absence of an aromatic promoter, it is preferred to exclude the presence of steam therefrom.

The temperature at which the alcohol and/or ether hydrocarbon conversion process is conducted should be minimized to limit the rate of coke build-up. Accordingly, the temperature of the reaction zone typically will vary from about 300° to about 350°, preferably from about 320° to about 340°, and most preferably from about 325° to about 340° C. If the reaction temperature exceeds about 375° C. the rate of coke deposition is so fast the benefits of the 2-stage treatment to a large extent are lost.

The reaction feed may be passed over the catalyst at a contact time with the catalyst sufficient to achieve a WHSV of typically from about 2 to about 10, preferably from about 2 to about 7, and most preferably from about 2.5 to about 4 $hr^{-1}$. The reaction pressure typically will be controlled to about 1 atmosphere. Excessively high pressures alter reaction rates and coking increases significantly.

Although the advantages provided by the catalyst pretreatment of the present invention vis-a-vis the production of olefins at high selectivity and increased catalyst life are not negated by operating under a combination of conditions which does not convert all of the feed, it is most advantageous to select the combination of temperature, feed rate and pressure conditions such that at least 60 weight percent of the feed is converted to hydrocarbons, and it is particularly preferred to select the combination of conditions so that substantially complete feed conversion is in fact achieved. Furthermore, it is particularly desired to use conditions in the specified ranges that produce conversion to a hydrocarbon mixture comprising a major fraction by weight of olefin. More importantly, however, it is essential to employ the low reaction temperatures described herein which favor olefin production in order to observe the improvement in catalyst life resulting from the two-stage zeolite modification. This is based on the conclusion that at low reaction temperatures the acidity characteristics of the external surface of the modified zeolite is the primary controlling factor in the rate of coke production. However, as the reaction temperature increases above about 375° C., these characteristics, as a coke rate controlling factor, diminish in effect to the extent that coke formation becomes uncontrollable. Thus, the present invention resides not only in the two-stage zeolite modification but also in the use of the modified zeolite in conjunction with specifically defined hydrocarbon conversion temperature regime.

The reaction product effluent from the hydrocarbon conversion process of the present invention contains a hydrocarbon mixture particularly rich in the light olefins, ethylene and propylene, as well as some aromatic hydrocarbons. Generally, a major fraction of the total olefins, calculated on a mol basis, is ethylene plus propylene. The predominant aromatic hydrocarbons are monocyclic hydrocarbons, notably $C_8$ and $C_9$ aromatics. Thus, the predominant hydrocarbons are all valuable petrochemicals. The hydrocarbons are separated from one another by methods well known in the art.

The following examples are given as specific illustrations of the claimed invention. It should be understood, however, that the invention is not limited to the specific details set forth in the examples. All parts and percentages in the examples as well as in the remainder of the specification are by weight unless otherwise specified.

Unless otherwise specified, catalyst acidity measurements described herein are determined by measuring the ammonia adsorption of a catalyst sample on a Perkin Elmer TGS-II thermogravimetric analyzer using the following procedure:

1. Tare a clean dry platinum sample pan.
2. Add sample (10–20 mg) to the pan and place the pan on the TGS-II balance.
3. Set a flow of 40 ml/min of dry, ultrapure $N_2$ through the top section of the balance and 30 ml/min of the same $N_2$ through the sample chamber.
4. Heat the sample to 500° C. in $N_2$ for 30 minutes to dry it and desorb any materials.
5. Set the furnace temperature to a value of 325° C. at which a measurement is desired.
6. Allow the sample to come to a constant weight in the dry $N_2$ atmosphere and record the weight.
7. Change the gas flowing through the sample chamber to 2% $NH_3$ in $N_2$ with a flow rate of 30 ml/min.
8. Allow the sample to come to a constant weight and record the weight.

9.

$$\text{Wt. \% NH}_3 \text{ adsorbed} = \frac{\text{wt. in NH}_3 - \text{wt. in N}_2}{\text{wt. in N}_2} \times 100$$

EXAMPLE 1

The following example illustrates the preparation of a crystalline aluminosilicate of the ZSM-5 type by 2 different methods. The zeolite catalysts prepared by each method are designated Catalyst-A, Catalyst-B, for ease of discussion and are employed in subsequent examples.

PART A

Preparation of Catalyst-A

A solution containing 10.8 g (0.041 mole) tetrapropylammonium bromide (TPAB) dissolved in 20 g (1.11 mole) water was added to 155.6 g (0.79 mole) of aqueous collodial silica solution to form Solution 1.

A second solution was prepared by dissolving 10.2 g (0.255 mole) NaOH in 20 g (1.11 mole) water. A third solution was prepared by dissolving 1.0 g (0.0046 mole) of sodium aluminate in 20 g (1.11 moles) of water. Solution 2 was then added to Solution 1 to form a fourth solution followed by the addition of Solution 3 to Solution 4 to form a reaction mixture.

The reaction mixture was placed in a Teflon lined autoclave and heated at 100° C. for 6 days without stirring. The solid white reaction product was cooled to room temperature, filtered, washed with deionized water, and dried in an oven at 110° C. for about 18 hours. The dried product was then calcined in air in an oven at 550° C. for 4 hours.

The calcined zeolite was then subjected to ion exchange using a NH$_4$NO$_3$ solution. The ion exchange procedure was conducted 4 times successively. In each successive exchange, the calcined zeolite was mixed with an aqueous solution of 1N NH$_4$NO$_3$ in an amount of 20 cc of solution per gram of zeolite and the mixture allowed to soak for 4 to 5 hours at room temperature. Upon completion of the last ion-exchange the zeolite was washed with water, dried in air for about 18 hours at 110° C., and then re-calcined at 550° C. in air for between 4 and 5 hours in a forced hot air oven. The resulting zeolite contained 0.9 wt.% Al; 86.35 wt.% SiO$_2$; 1.72 wt.% Al$_2$O$_3$; and 0.4 wt.% Na$_2$O. The X-ray diffraction pattern corresponds to ZSM-5 and the zeolite possesses a crystallinity of about 69% as determined from indexing the peak heights of the reflection 20-23.1 compared to a silicalite standard. The acid content of catalyst Sample A was determined, by the ammonia adsorption method described herein, to be characterized by an acid site number of 76 meq/g. The effective silica to alumina mole ratio was calculated to be 120, from an actual silica:alumina mole ratio of 85 and the aforedescribed sodium content.

PART B

(Preparation of Catalyst Sample B)

Three solutions were prepared as follows: Solution 1 was prepared by mixing 15.21 g of colloidal silica (Ludox AS 40 TM) with 45 g N-tetrapropylammonium hydroxide. Solution 2 was prepared by dissolving 0.21 g of Al(NO$_3$)$_3$9H$_2$O in 5 ml water. Solution 2 was then added to Solution 1. The pH of the reaction mixture was then adjusted to 11.5 by the addition of an aqueous 1N solution of HNO$_3$. The reaction mixture was then placed in a Teflon liner and placed in an autoclave under 50 psig nitrogen. The autoclave was heated to 150° C. for 6 days without stirring. The autoclave was then cooled down to room temperature and the solid product was filtered and washed with 800 ml distilled water. The product was then dried in the vacuum oven at 120° C. for sixteen hours and then calcined at 550° C. with a stream of air. X-ray analysis showed the material to be highly crystalline ZSM-5 type aluminosilicate.

The calcined zeolite was analyzed and found to contain 0.240 wt.% Al; 44.83 wt.% Si; and 418 ppm Na. The crystallinity (determined in accordance with Part A) of the zeolite was found to be 104%. The acid content was found by ammonia adsorption to be 88 meq/g at 325° C. The effective and actual silica:alumina mole ratio was found to be 360:1. The X-ray diffraction pattern of the calcined zeolite corresponds to ZSM-5.

EXAMPLE 2

Each of catalyst Samples A and B were the subjected to the two stage modification and tested in numerous runs as follows:

About 1.0 g of each catalyst sample was placed in a tubular reactor described hereinafter in conjunction with catalyst testing.

The reactor was then heated to a suitable coke precursor forming temperature as described at Table 1, and a coke precursor forming hydrocarbon, i.e. methanol, was passed therethrough at a rate sufficient to achieve a WHSV in hr$^{-1}$ as shown at Table 1. The duration of the step is also provided at Table 1.

Upon completion of coke precursor forming step, the feed of the coke precursor hydrocarbon (methanol) was discontinued and the feed line and reactor were purged of any methanol until none exits the reactor. The furnace temperature was then increased to the heat conditioning conditions and the heat conditioning step conducted. Accordingly, the heat conditioning gas, i.e. N$_2$ was passed through the reactor under the conditions shown at Table 1.

Upon completion of the heat conditioning step, the furnace temperature was reduced to reaction temperature and the catalyst was tested. Accordingly, a feed gas mixture as described at Table 1 was introduced into a tubular reactor at the conditions shown at Table 1.

Unless otherwise specified, the testing of the zeolites prepared as described herein is conducted in a tube reactor comprising a stainless steel tube having the dimensions: length 36 cm, O.D. 1.27 cm, and I.D. 1.0 cm. The tube is employed in a verticle position. Across the bottom opening thereof is placed a wire mesh screen on top of which is placed glass wool. About 1 cc of inert alumina particles (−30+80 mesh) are placed on top of the glass wool. About 1 g (e.g. about 1 cc) of each zeolite tested is then inserted on top of the glass wool and covered with the same, followed by about 1 cc of alumina particles, on top of which is placed more glass wool. The reactant feed is passed through the top of the reactor and the products collected from the bottom. Reactor effluent samples are analyzed by on line gas chromatography at the designated on stream times. Inlet lines to the reactor are placed in a hot box where any liquid feed is vaporized. The reactor is heated in a radiant I.R. furnace and the reaction temperature is determined from thermocouples placed in the upper zone of alumina particles.

In Table 1, Runs 4 to 7, 17 to 18, and 22 to 36 employ a zeolite which has been subjected to the two stage treatment described herein, while Runs 1 to 3, 8 to 15, and 19 to 21, were not and are included for comparative purposes. In addition, Runs 19 to 24 and 29 to 30 employ a feed gas for olefin formation of methanol and toluene at a mole ratio thereof of 9:1 respectively. Runs 31 to 33 employ a feed gas for olefin formation of methanol/toluene/H₂O at a mole ratio thereof of 9:1:2.5 respectively. Runs 34 to 36 employ a feed gas for olefin formation of methanol/p-xylene/H₂O of 9:1:2.5 respectively.

As used herein the following terms are calculated as follows on a carbon % basis:

$$\text{Selectivity (\%)} = \frac{nC_n}{\sum_{1 \to i} nC_n} \times 100$$

wherein $C_n$ is a hydrocarbon product (excluding dimethylether) having n carbon atoms; and i is the maximum number of carbon atoms of any compound in the product.

$$\text{Conversion (\%)} = \frac{\text{Total No. of Carbon Atoms in Product}}{\text{Total No. of Carbon Atoms in Feed}} \times 100$$

$$\text{Yield (\%)} = \frac{\text{Selectivity} \times \text{Conversion}}{100}$$

In Table 1, when an on-stream time is reported in conjunction with a conversion, such on-stream time represents the reaction time needed to first achieve this conversion.

TABLE 1

| COL 1 | COL 2 | COL 3 | COL 4 | COL 5 | COL 6 | COL 7 | COL 8 | COL 9 | COL 10 | COL 11 |
|---|---|---|---|---|---|---|---|---|---|---|
| | | | COKE PRECURSOR FORMING CONDITIONS | | | | HEAT CONDITIONING STEP | | | |
| EX. OR C. EX. NUMBER | RUN NO. | CATALYST SAMPLE TYPE | COKE PRECURSOR FORMING FEED TYPE | TEMP. (°C.) | FLOW RATE (WHSV) | TREATING TIME (HRS.) | GAS FEED TYPE | TEMP. (°C.) | FLOW RATE (ml/min) | HEAT COND. TIME (HRS.) |
| C. EX. 1 | 1 | A | N/A | → | → | → | → | → | → | → |
| | 2 | A | N/A | → | → | → | → | → | → | → |
| | 3 | A | N/A | → | → | → | → | → | → | → |
| EX. 1 | 4 | A | MeOH | 335 | 3.7 | 1-2 | N₂ | 400 | 30 | 2 |
| | 5 | A | MeOH | 335 | 3.7 | 1-2 | N₂ | 400 | 30 | 2 |
| | 6 | A | MeOH | 335 | 3.7 | 1-2 | N₂ | 400 | 30 | 2 |
| | 7 | A | MeOH | 335 | 3.7 | 1-2 | N₂ | 400 | 30 | 2 |
| C. EX. 2 | 8 | B | N/A | → | → | → | → | → | → | → |
| | 9 | B | N/A | → | → | → | → | → | → | → |
| | 10 | B | N/A | → | → | → | → | → | → | → |
| | 11 | B | N/A | → | → | → | → | → | → | → |
| C. EX. 3 | 12 | B | N/A | → | → | → | → | → | → | → |
| | 13 | B | N/A | → | → | → | → | → | → | → |
| | 14 | B | N/A | → | → | → | → | → | → | → |
| | 15 | B | N/A | → | → | → | → | → | → | → |
| EX. 2 | 16 | B | MeOH | 335 | 3.7 | 1-2 | N₂ | 375 | 30 | 3 |
| | 17 | B | MeOH | 335 | 3.7 | 1-2 | N₂ | 375 | 30 | 3 |
| | 18 | B | MeOH | 335 | 3.7 | 1-2 | N₂ | 375 | 30 | 3 |
| C. EX. 4 | 19 | B | N/A | → | → | → | → | → | → | → |
| | 20 | B | N/A | → | → | → | → | → | → | → |
| | 21 | B | N/A | → | → | → | → | → | → | → |
| EX. 3 | 22 | B | MeOH | 335 | 3.7 | 1.5-2 | N₂ | 375 | 30 | 2 |
| | 23 | B | MeOH | 335 | 3.7 | 1.5-2 | N₂ | 375 | 30 | 2 |
| | 24 | B | MeOH | 335 | 3.7 | 1.5-2 | N₂ | 375 | 30 | 2 |
| EX. 4 | 25 | B | MeOH | 335 | 3.7 | 1.5-2 | N₂ | 400 | 30 | 2 |
| | 26 | B | MeOH | 335 | 3.7 | 1.5-2 | N₂ | 400 | 30 | 2 |
| | 27 | B | MeOH | 335 | 3.7 | 1.5-2 | N₂ | 400 | 30 | 2 |
| EX. 5 | 28 | B | MeOH | 335 | 3.7 | 1.5-2 | N₂ | 400 | 30 | 2 |
| | 29 | B | MeOH | 335 | 3.7 | 1.5-2 | N₂ | 400 | 30 | 2 |
| | 30 | B | MeOH | 335 | 3.7 | 1.5-2 | N₂ | 400 | 30 | 2 |
| EX. 6 | 31 | B | MeOH | 335 | 3.7 | 1.5-2 | N₂ | 400 | 30 | 2 |
| | 32 | B | MeOH | 335 | 3.7 | 1.5-2 | N₂ | 400 | 30 | 2 |
| | 33 | B | MeOH | 335 | 3.7 | 1.5-2 | N₂ | 400 | 30 | 2 |
| EX. 7 | 34 | B | MeOH | 335 | 3.7 | 1.5-2 | N₂ | 400 | 30 | 2 |
| | 35 | B | MeOH | 335 | 3.7 | 1.5-2 | N₂ | 400 | 30 | 2 |
| | 36 | B | MeOH | 335 | 3.7 | 1.5-2 | N₂ | 400 | 30 | 2 |

| COL 1 | COL 2 | COL 3 | COL 12 | COL 13 | COL 14 | COL 15 | COL 16 | COL 17 | COL 18 | COL 19 | COL 20 |
|---|---|---|---|---|---|---|---|---|---|---|---|
| EX. OR C. EX. NUMBER | RUN NO. | CATALYST SAMPLE TYPE | REACTION CONDITIONS | | | | | | | CONVERSION | YIELD |
| | | | FEED STREAM TYPE | FLOW RATE (WHSV) | TEMP. (°C.) | HOURS ON STREAM | SELECTIVITY % | | | SION (%) | % |
| | | | | | | | $C_2^=$ | $C_3^=$ | $C_2^= + C_3^=$ | | $C_2^= + C_3^=$ |
| C. EX. 1 | 1 | A | MeOH | 3.7 | 335 | 1 | 44 | 26 | 70 | 66 | 46.2 |
| | 2 | A | MeOH | 3.7 | 335 | 5 | 37 | 35 | 72 | 26 | 18.7 |
| | 3 | A | MeOH | 3.7 | 335 | 10 | 42 | 31 | 73 | 13 | 9.5 |
| EX. 1 | 4 | A | MeOH | 3.7 | 335 | 3 | 25 | 25 | 50 | 100 | 50.0 |
| | 5 | A | MeOH | 3.7 | 335 | 7 | 31 | 29 | 60 | 92 | 55.2 |
| | 6 | A | MeOH | 3.7 | 335 | 17 | 28 | 28 | 56 | 71 | 39.8 |
| | 7 | A | MeOH | 3.7 | 335 | 21 | 38 | 37 | 75 | 38 | 28.5 |

TABLE 1-continued

|  | Run | Catalyst | Feed | WHSV | Temp (°C) | Time (hr) | Col 8 | Col 9 | Col 10 | Col 11 | Col 12 |
|---|---|---|---|---|---|---|---|---|---|---|---|
| C. EX. 2 | 8 | B | MeOH | 3.7 | 250 | 5 | 23 | 16 | 39 | 100 | 39.0 |
|  | 9 | B | MeOH | 3.7 | 250 | 10 | 26 | 15 | 41 | 100 | 41.0 |
|  | 10 | B | MeOH | 3.7 | 250 | 15 | 33 | 16 | 49 | 100 | 49.0 |
|  | 11 | B | MeOH | 3.7 | 250 | 25 | 39 | 23 | 62 | 82 | 14.3 |
| C. EX. 3 | 12 | B | MeOH | 3.7 | 335 | 5 | 31 | 16 | 47 | 100 | 47.0 |
|  | 13 | B | MeOH | 3.7 | 335 | 10 | 36 | 18 | 54 | 100 | 54.0 |
|  | 14 | B | MeOH | 3.7 | 335 | 20 | 36 | 17 | 53 | 100 | 53.0 |
|  | 15 | B | MeOH | 3.7 | 335 | 27 | 38 | 23 | 61 | 90 | 55.0 |
| EX. 2 | 16 | B | MeOH | 3.7 | 335 | 4 | 37 | 15 | 52 | 100 | 52.0 |
|  | 17 | B | MeOH | 3.7 | 335 | 20 | 34 | 16 | 50 | 100 | 50.0 |
|  | 18 | B | MeOH | 3.7 | 335 | 37 | 38 | 23 | 61 | 90 | 55.0 |
| C. EX. 4 | 19 | B | MeOH/T | 3.7 | 335 | 6 | 41 | 16 | 57 | 100 | 57.0 |
|  | 20 | B | MeOH/T | 3.7 | 335 | 24 | 45 | 29 | 74 | 60 | 44.4 |
|  | 21 | B | MeOH/T | 3.7 | 335 | 38 | 46 | 31 | 77 | 42 | 32.3 |
| EX. 3 | 22 | B | MeOH/T | 3.7 | 335 | 9 | 42 | 17 | 59 | 100 | 59.0 |
|  | 23 | B | MeOH/T | 3.7 | 335 | 25 | 45 | 26 | 71 | 80 | 56.8 |
|  | 24 | B | MeOH/T | 3.7 | 335 | 36 | 45 | 31 | 76 | 48 | 23.56 |
| EX. 4 | 25 | B | MeOH | 3.7 | 335 | 4 | 37 | 15 | 52 | 100 | 52.0 |
|  | 26 | B | MeOH | 3.7 | 335 | 20 | 34 | 16 | 50 | 100 | 50.0 |
|  | 27 | B | MeOH | 3.7 | 335 | 37 | 38 | 23 | 61 | 90 | 54.9 |
| EX. 5 | 28 | B | MeOH/T | 3.7 | 335 | 5 | 41 | 16 | 57 | 100 | 57.0 |
|  | 29 | B | MeOH/T | 3.7 | 335 | 10 | 46 | 25 | 71 | 90 | 63.9 |
|  | 30 | B | MeOH/T | 3.7 | 335 | 13 | 46 | 31 | 77 | 50 | 38.5 |
| EX. 6 | 31 | B | MeOH/T/$H_2O$ | 3.7 | 335 | 6 | 41 | 16 | 57 | 100 | 57.0 |
|  | 32 | B | MeOH/T/$H_2O$ | 3.7 | 335 | 24 | 45 | 29 | 74 | 60 | 44.4 |
|  | 33 | B | MeOH/T/$H_2O$ | 3.7 | 335 | 38 | 46 | 31 | 77 | 42 | 32.3 |
| EX. 7 | 34 | B | MeOH/P-X/$H_2O$ | 3.7 | 335 | 14 | 46 | 20 | 66 | 100 | 66.0 |
|  | 35 | B | MeOH/P-X/$H_2O$ | 3.7 | 335 | 24 | 47 | 24 | 71 | 95 | 67.4 |
|  | 36 | B | MeOH/P-X/$H_2O$ | 3.7 | 335 | 60 | 49 | 33 | 82 | 40 | 32.8 |

N/A = NOT APPLICABLE
MeOH = METHANOL
T = TOLUENE
P-X = PARA-XYLENE

DISCUSSION OF RESULTS

Runs 1 to 3 of Comparative Example 1 illustrate the performance of an untreated zeolite. Comparing these runs with Runs 4 to 7 of Example 1 it can be seen that the catalyst life, in terms of conversion, is more than doubled by the 2-stage treatment employed for Runs 4 to 7, e.g. compare Run 3 (10 hr on-stream time at 13% conversion) with Run 7 (21 hr on-stream time at 38% conversion). While olefin selectivity is slightly reduced during the early stages of reaction for Example 1, this reduction is more than compensated for by higher conversions and enhanced olefin yields.

Runs 8 to 11 of Comparative Example 2 illustrate the effect of employing a methanol conversion reaction temperature of 250° C. on an untreated catalyst Sample B. Runs 12 to 15 of Comparative Example 3 employ the same type of untreated catalyst Sample B, but at a reaction temperature of 335° C. Contrasting Comparative Examples 2 and 3 it can be seen that the catalyst life decays faster for Comparative Example 2 than for Comparative Example 3, e.g. compare Runs 11 and 15 wherein in Run 11 the conversion has dropped to 82% after 25 hours, while in Run 15 the conversion has dropped to only 90% after 27 hours. Note also the enhanced selectivity of Comparative Example 3. It is believed that a reaction temperature of at least about 300° C. is needed to achieve a desirably rapid conversion of dimethylether, formed from the methanol feed, to olefins and higher carbon number products. Thus, the hydrocarbon feed in contact with the catalyst of Comparative Example 2 is richer in dimethylether content than Comparative Example 3. Such a high DME content during the early stages of reaction is therefore believed to be detrimental to the catalyst life, even in the absence of the 2-stage treatment described herein.

Comparing Runs 16 to 18 of Example 2 with the runs of Comparative Examples 2 and 3 it can be seen that the 2-stage treated catalyst of Example 2 increases the catalyst life by 10 hours relative to Comparative Example 3 (i.e. it takes 10 hours longer for conversion to drop to 90%) and even more relative to Comparative Example 2, while maintaining the olefin selectivities of Comparative Example 3.

Runs 19 to 21 of Comparative Example 4 illustrate the effect of employing an aromatic promoter (i.e. toluene) in the feed in addition to methanol, when using a catalyst Sample B which has not been pretreated. Contrasting Comparative Example 4 with Comparative Example 3 it can be seen that olefin selectivity is enhanced at the expense of conversion by the inclusion of an aromatic promoter. Runs 22 to 24 of Example 3 employ the same promoter as Comparative Example 4 but in conjunction with a pre-conditioned catalyst. Comparing the runs of Example 3 with those of Comparative Example 4 it can be seen that although an improvement in catalyst life is achieved, e.g., compare Run 23 with Run 20, the improvement after 36 hours of reaction time (compare Runs 24 and 21) is less pronounced than in the absence of a promoter, e.g. compare also Examples 4 and 5. However, when water is added to the methanol/toluene feed as per Runs 31 to 33 of Example 6 a substantial increase in catalyst life is achieved relative to Example 5 (in the absence of water). Runs 34 to 36 of Example 7 illustrate an even greater enhancement in catalyst life when the toluene of Example 6 is replaced by p-xylene.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for converting an alcohol and/or ether feed as hereinafter defined to a hydrocarbon mixture rich in olefins which comprises contacting, under conversion conditions at a conversion reaction temperature of from about 300° to 350° C., a feed comprising one or more monohydric alcohols having from about 1 to about 4 carbon atoms, ethers derived therefrom, or mixtures of said alcohols and ethers, with a modified crystalline metalosilicate shape selective acidic zeolite, wherein said metalosilicate is selected from the group consisting of aluminum, gallium, and mixtures thereof, and wherein said zeolite, prior to modification and in the absence of any coke deposited thereon, possesses:

(a) the capability of catalyzing said alcohol and/or ether conversion reaction;
    (b) a channel size and structure such as to permit (i) entry of the said feed into the zeolite and diffusion to the active acid sites within said zeolite, and (ii) formation of olefin products within said zeolite and diffusion of said products out of the zeolite; and
    (c) hydrothermal stability at temperatures of at least about 290° C.; and wherein the modification of said zeolite is conducted in a manner sufficient to increase the catalyst life of said zeolite, relative to the absence of said modification when said zeolite is employed as a catalyst for said alcohol and/or ether conversion reaction, by a process comprising:
    (A) contacting said zeolite with coke precursor forming feed for a period of from about 0.5 to about 4 hours, said coke precursor forming feed being (i) comprised of at least one member selected from the group consisting of monohydric alcohols having from 1 to about 4 carbon atoms, ethers derived from said alcohols, olefins having from about 1 to about 5 carbon atoms, and mixtures thereof; and (ii) heated to a temperature of from about 320° to about 350° C.; and
    (B) contacting the zeolite, treated in accordance with Step (A), with an inert gas heated to a temperature of from about 350° to about 425° C. for a period of at least 1 hour.

2. The process of claim 1 wherein Step (A) of the zeolite modification is conducted by contacting said zeolite with a vaporized coke precursor forming feed selected from the group consisting of ethylene, propylene, butene, methanol, propanol, butanol, dimethyl ether and mixtures thereof, at a temperature of from about 330° to about 340° C. for a period of from about 1 to about 2 hours.

3. The process of claim 2 wherein in Step (B) the inert gas is selected from the group consisting of nitrogen, helium, argon, carbon dioxide and mixtures thereof.

4. The process of claim 3 wherein in Step (A) of the zeolite modification said coke precursor forming feed is methanol, and said inert gas in Step (B) is nitrogen.

5. The process of claim 1 wherein the zeolite which is modified is ZSM-5.

6. The process of claim 1 wherein the alcohol and/or ether feed comprises methanol in the absence of steam.

7. The process of claim 1 wherein the alcohol and/or ether feed comprises dimethyl ether.

8. The process of claim 7 wherein the alcohol and/or ether feed contains steam in an amount sufficient to provide a mole ratio of dimethyl ether to steam therein of from about 1:5 to about 1:0.2.

9. The process of claim 1 wherein the alcohol and/or ether feed comprises methanol, at least one aromatic promoter capable of increasing the selectivity of the hydrocarbon conversion reaction to olefins relative to its absence, and water in an amount sufficient to increase the catalyst life of the zeolite relative to its absence.

10. The process of claim 9 wherein the aromatic promoter is selected from the group consisting of toluene, p-xylene, benzene and mixtures thereof.

11. The process of claim 10 wherein the mole ratio of methanol:aromatic promoter:water in the hydrocarbon feed is from about 1:0.2:0.5 to about 1:0.01:0.05.

* * * * *